United States Patent [19]

Sanderson et al.

[11] 4,440,870

[45] Apr. 3, 1984

[54] NOVEL BORATE CATALYST SYSTEMS

[75] Inventors: John R. Sanderson; Lewis W. Watts, Jr.; Walter H. Brader, Jr., all of Austin, Tex.

[73] Assignee: Texaco Inc., White Plains, N.Y.

[21] Appl. No.: 402,661

[22] Filed: Jul. 28, 1982

[51] Int. Cl.³ .............................................. B01J 21/02
[52] U.S. Cl. ................................................... 502/207
[58] Field of Search ........................................ 252/432

[56] References Cited

U.S. PATENT DOCUMENTS

| | | | |
|---|---|---|---|
| 2,193,814 | 3/1940 | Heard | 252/432 |
| 3,470,030 | 9/1969 | Lindholm et al. | 252/432 X |
| 3,789,065 | 1/1974 | Kollar | 210/497 R |
| 3,836,452 | 9/1974 | Gleim | 252/432 X |
| 4,012,423 | 3/1977 | Brownstein et al. | 260/348 R |
| 4,033,901 | 7/1977 | Beinicky et al. | 252/432 |
| 4,069,381 | 1/1978 | Gaenzler et al. | 560/1 |
| 4,220,800 | 9/1980 | Stapp | 560/246 |
| 4,239,911 | 12/1980 | Weitz et al. | 560/246 |
| 4,256,650 | 3/1981 | Bljumberg et al. | 260/348.33 |

*Primary Examiner*—William G. Wright
*Attorney, Agent, or Firm*—Jack H. Park; Kenneth R. Priem; David L. Mossman

[57] ABSTRACT

Novel borate catalyst systems useful for the esterification of olefins are described. The catalyst system is made up of two or more transition metal borates which are co-precipitated. Typical are the zirconyl-cobalt borate, zirconyl-nickel borate and vanadyl-cobalt borate systems.

3 Claims, No Drawings

4,440,870

NOVEL BORATE CATALYST SYSTEMS

CROSS-REFERENCES TO RELATED APPLICATIONS

This application is related to U.S. patent application Ser. No. 402,664, and U.S. patent application Ser. No. 402,663, which concern methods for producing alkane acetates by oxidative esterification of olefins over transition metal borate catalysts. Thallium borates are used as catalysts in U.S. patent application Ser. No. 402,665, alkali metal borates are the catalysts in U.S. patent application Ser. No. 402,668, and alkali earth metal borates are the catalysts in U.S. patent application Ser. No. 402,667, all in the same or similar reactions. All of these patent applications are filed on July 28, 1982.

BACKGROUND OF THE INVENTION

1. Field of the Invention

The invention is related to borate catalyst systems and is more particularly related to transition metal borate catalyst systems useful in the esterification of olefins.

2. Description of Other Relevant Catalysts in the Field

A number of different catalysts have been used to produce propylene oxide from propylene or to produce an intermediate to propylene oxide from propylene have been proposed. Initially the research effort seemed to be directed to producing an olefin oxide directly from the olefin in the presence or absence of a solvent. U.S. Pat. No. 2,649,463 describes the production of a coordination complex created by the reaction of an olefin with a metal halide where the metal is copper, platinum, palladium, iridium, aluminum, zinc, silver, mercury or antimony. This coordination complex is further reacted with oxygen at a high temperature to produce the olefin oxide plus oxygen-containing metal halides. Hawkins, et al. in an article entitled, "Autoxidation of Olefins," in the *Journal of Applied Chemistry*, Vol. 6, 1956, pgs 1 through 10, describes a process for the production of epoxides directly from olefins and molecular oxygen over magnesium oxide and/or cobalt naphthenate. The direct production of olefin oxides from a mono olefin and a saturated hydrocarbon with oxygen and water, organic acids or olefin oxide in low concentration is described in U.S. Pat. No. 2,780,634.

British Pat. No. 1,582,261 describes how propylene may be reacted with oxygen over a dinitrogen tetraoxide catalyst in a liquid medium of a chlorinated organic solvent to produce propylene oxide directly. Propylene oxide may also be prepared directly from propylene and oxygen over a catalyst system comprising a palladium cation plus a chloride anion in the presence of a phosphorous or arsenic ligand as revealed in U.S. Pat. No. 4,256,649.

Further, U.S. Pat. No. 2,784,202 outlines how propylene in a liquid hydrocarbon solvent, such as benzene, in the presence of oxygen and water, organic acids or propylene oxide in low concentration yield propylene oxide when heated at a temperature between 130° and 300° C. Propylene oxide is also proposed to be made directly from propylene in benzene in the presence of oxygen over a cobalt, copper, magnesium, vanadium or chromium catalyst where barium or lead is used as a promoter for the catalyst, according to U.S. Pat. No. 3,071,601. Brill, et al. in *Journal of Organic Chemistry*, Vol. 29, 1964, pgs 140-143, describes a process for passing olefins and oxygen, frequently in contact with or dissolved in benzene over various catalysts such as azobisisobutyronitrile, cadmium oxide, cobaltic acetylacetonate, magnesium oxide or methyl ethyl ketone peroxide to produce various oxidation products, including the desired epoxides. U.S. Pat. No. 3,132,156 reveals that ethylene, propylene or butylene oxide may be produced directly from ethane, propane or butane under very precise conditions. These conditions include a temperature of between 425° to 575° C., an oxygen volume percent of between 4 and 14, a contact time with the oxygen of between 0.07–1.5 seconds, a pressure of between 20 to 150 psig and constant concentrations of reactants. Epoxides may also be produced from olefins and oxygen which are in an inert reaction medium when they are brought in contact with a rhenium catalyst and 0.05 to 15 weight percent of a reaction modifier comprised of an alkyl aryl or cyclo alkyl cyanide, pyridine or quinoline in accordance with the invention described in U.S. Pat. No. 3,316,279.

Other schemes for producing olefin oxides from olefins and oxygen by means of a solvent or liquid reaction medium include the following. U.S. Pat. No. 3,153,058 employs polyacyl esters of polyhydroxy alkanes, polyhydroxy cycloalkanes, polyglycols or mixtures thereof as the solvent. Materials selected from saturated aliphatic, alicyclic and aromatic nitriles and mixtures thereof form the solvent in U.S. Pat. No. 3,210,380. Boric acid esters form the liquid reaction medium in U.S. Pat. No. 3,210,381. U.S. Pat. No. 3,228,967 uses major amounts of acetone as the solvent. Carbonic acid esters are employed in U.S. Pat. No. 3,228,968, and at least 25 percent by weight of certain ketones serves as the reaction medium in U.S. Pat. No. 3,232,957. Halogenated benzenes serve as the solvent in U.S. Pat. No. 3,238,229 while benzoic acid esters are employed in a similar reaction described in U.S. Pat. No. 3,281,433. Olefin oxides may be prepared directly from olefins and oxygen over a hydrocarbon soluble, phosphorous molybdenum-hydroxy compound catalyst according to the disclosure in U.S. Pat. No. 3,856,826. The approach of making epoxides directly has never been commercially feasible because all of the methods explored gave low yields of epoxides.

At this point in the history of this research, the emphasis seems to shift from making the olefin oxides directly to making an intermediate which could be converted to the olefin oxides by a second step. For example, U.S. Pat. No. 2,497,408 suggests the production of propylene glycol diacetate from propylene, oxygen and acetic acid over a metal acetate catalyst in which the metal is lead or iron in combination with an alkali earth metal acetate. Another example of this latter approach is U.S. Pat. No. 3,403,175 where olefins in oxygen are reacted in the presence of a reaction medium consisting of carboxylic acid and anhydrides with no catalyst to produce glycol diesters. Acyloxy compounds, which are intermediates to olefin epoxides, may be produced by the reaction of olefins with the metal salt of a carboxylic acid in an aqueous solution if electric current is passed through the solution, according to the method of U.S. Pat. No. 3,453,189. U.S. Pat. No. 3,479,395 reveals that olefins in oxygen may be converted to glycols and glycol acetates by being brought into contact with a solution comprising tellurium dioxide, an alkali metal halide and a redox agent dissolved in a solvent of certain specifications (water, acetic acid, dioxane, dialkyl formamides or dialkyl sulfoxides).

Further examples of the approach to making intermediates to the epoxides include U.S. Pat. No. 3,542,857 where vicinal glycol monoesters and diesters may be made by passing olefins in oxygen in an alkanoic acid medium over cerium salts. A method for making glycol esters from olefins and oxygen in a carboxylic acid medium over tellurium and an appropriate form of bromine is revealed in U.S. Pat. No. 3,668,239. British Pat. No. 1,278,353 teaches that nonvicinal glycols may be reacted with carbon monoxide over a rhodium or iridium catalyst together with a halogen promoter to produce dicarboxylic acids which are precursors to diesters which are intermediates to the epoxides. Further, British Pat. No. 1,326,219 discloses that glycol esters may be produced from olefins and oxygen in the presence of at least one carboxylic acid when a halogen is employed as an anion and a metal cation is present which is selected from the group of tellurium, cerium, antimony, manganese, arsenic or cobalt. Other examples which reveal how esters may be made from olefins include U.S. Pat. No. 3,770,813 where an olefin with a chloro, hydroxy or lower alkanoyloxy substituent together with oxygen and a monobasic carboxylic acid may be reacted together over an iodide anion and a heavy metal cation of atomic numbers 21 to 30 and 48, and nitrogen-containing cations to give glycol esters. Olefins and oxygen may be reacted together over a catalyst system comprising a metal cation of tellurium, cerium, antimony, vanadium, gallium, arsenic, copper, selenium or silver with a bromine or chlorine anion to produce vicinal glycol esters which are later fractionated to give a residue with a boiling point higher than the vicinal glycol esters according to the disclosure in U.S. Pat. No. 3,789,065. The residue is then contacted with a carboxylic acid to yield additional vicinal glycol esters. British Pat. No. 1,353,814 describes the reaction of olefins and oxygen in a carboxylic acid in the liquid phase that contains at least 0.5 percent water over a catalyst system identical to that of the patent previously described to also yield vicinal glycol esters. Ethylene or propylene may be reacted with oxygen in a carboxylic acid over a catalyst system comprising a tellurium cation and a bromide anion or a selenium cation plus a chloride or bromide anion to produce vicinal glycol esters as revealed in U.S. Pat. No. 3,907,874.

Aliphatic hydrocarbon carboxylic acid esters of vicinal glycols which contain organic halogen impurities may be purified by passing them over aquobasic alkali metal compounds, aquobasic earth metal compounds or compounds (other than halides) of zinc, lead, cadmium, tin, mercury, silver, manganese, copper, nickel, cobalt, iron or chromium in accordance with the invention in British Pat. No. 1,410,834. German Auslegeschrift No. 2,430,022 describes a multi-step procedure for producing butane diols, which are precursors to butane oxide, from propylene, oxygen and acetic acid.

A system which has obtained a fair amount of commercial importance is described in U.S. Pat. No. 4,045,477 by which vicinal hydroxy esters and diesters are produced from olefins and oxygen over tellurium and an iodide source. Organic monoesters of vicinal glycols may also be produced from olefins, oxygen, water and a carboxylic acid over a system comprising an iodine compound (such as copper iodide, manganese iodide or cerium iodide), a copper compound, and an activated ion taken from the group of manganese, cerium, alkali metals, alkali earth metals, nitric compounds or mixtures thereof, according to the invention in U.S. Pat. No. 4,061,868. U.S. Pat. No. 3,069,381 reveals how glycol monoesters may be made from olefins, oxygen and carboxylic acids over a catalyst system where the cation is zirconium, niobium, molybdenum, hafnium, tantalum, tungsten or rhenium where the anion is a halide in the presence of lithium, sodium, potassium, titanium, vanadium, chromium, manganese, iron, cobalt, nickel, copper, zinc, aluminum or silver.

Some of the more recent patents in this field include the following. Esters may be produced from olefins in an acid plus oxygen over a tin or cerium catalyst in the presence of iodide as revealed by U.S. Pat. No. 4,154,957. Saturated vicinal esters may be produced from olefins, carboxylic acids and oxygen in the presence of a boron-containing catalyst according to the invention of U.S. Pat. No. 4,220,800. U.S. Pat. No. 4,221,916 teaches that olefins, carboxylic acids and oxygen when reacted together over a vanadium or ruthenium-containing catalyst can also produce saturated vicinal esters. U.S. Pat. No. 4,238,624 discloses a procedure by which ethylene, oxygen and a lower alkanoic acid are reacted together over an iodine source in a bismuth stabilized tellurium oxide catalyst on a carbon support to give ethylene glycol mono- and dialkanoates.

Further, alkylene glycol dicarboxalates may be made from carboxylic acid esters of monohydric or polyhydric short chain alcohols and olefins and oxygen over a catalyst system comprising tellurium, cerium, antimony, manganese, vanadium, gallium, arsenic or cobalt, plus a halogen anion and a hydrolyzing agent in addition to water as taught by U.S. Pat. No. 4,239,911.

Methods also exist for converting the ester intermediates into the epoxides. For example, U.S. Pat. No. 4,012,423 describes how vicinal hydroxy esters may be reacted over group I, II and IIIA basic metal carboxylates, being the preferred catalyst (sodium, potassium, lithium, calcium or barium, etc.), or group I, II and IIIA basic metal simple oxides and complex oxides and organic bases (such as borates, phosphates, oxides and carboxylates, particularly sodium borate, nickel oxide, etc.) to give epoxides. Another method is described in U.S. Pat. No. 4,158,008 whereby propylene glycol monoesters in the presence of a high boiling solvent is reacted over a base to produce propylene oxide. Propylene oxide may also be produced from propylene glycol with the removal of a water molecule over a weakly acidic carrier comprising a basic alkali metal salt of a low molecular weight carboxylic acid as taught by U.S. Pat. No. 4,226,780.

Of the numerous patents discussed so far, the ones considered to be most relevant to the invention at issue are U.S. Pat. Nos. 4,012,423; 4,069,381 and 4,220,800, all of which have been discussed.

Despite all of the investigative routes described so far and the ones that have been devised which have not been described, there is still a need for a catalyst for making propylene oxide from propylene, in addition to making the alkylene oxides from other olefins, which is not highly corrosive or highly expensive.

SUMMARY OF THE INVENTION

The invention concerns a catalyst system comprising at least two transition metal borates.

DETAILED DESCRIPTION OF THE PREFERRED EMBODIMENTS

Alkane hydroxy acetates and diacetates, also called glycol monoesters or diesters or vicinal diesters, may be prepared by the oxygen or air oxidation of olefins in a carboxylic acid and/or anhydride solvent in the presence of transition metal borate catalyst systems of this invention. The diacetates may be converted to epoxides or glycols using methods known in the art, some of which have been outlined previously. Both the epoxides and the glycols are of interest in the manufacture of important high volume products, including urethane polyols, gasoline additives, and heat transfer fluids. Borate compounds are novel for the catalysis of olefins to olefin acetates and diacetates (also called esters and diesters) never having been previously discovered.

The catalyst systems of this invention involve at least two transition metal borates. A transition metal is defined as an element from Groups IIIB, IVB, VB, VIB, VIIB, VIII, IB and IIB of the Periodic Table. It is preferred that the transition metal of the transition metal borates be taken from groups IIIB, IVB, VB, VIIB and VIII of the Periodic Table. Examples of such borates include vanadium borate, manganese borate, cobalt borate, nickel borate, yttrium borate and zirconyl borate. It is also preferred that at least one of the borates be a transition metal borate where the transition metal is taken from Group IVB or Group VB of the Periodic Table, especially zirconium and vanadium and that at least one of the borates be a transition metal borate where the transition metal is taken from Group VIII of the Periodic Table, especially nickel and cobalt. Especially preferred are the zirconyl borate/nickel borate combination, the vanadyl borate/cobalt borate combination and the zirconyl borate/cobalt borate combination. These catalysts are much less corrosive than many of those used in other methods of esterifying olefins, especially the halide systems. Also, much smaller catalyst levels may be used. They are also less expensive than many of the catalyst systems proposed for such esterification purposes.

The transition metal borates in the catalyst systems of this invention may be co-precipitated to provide the dual composition of the catalyst. Inorganic transition metal compounds may be dissolved in solution with borate compounds, such as sodium borate, to effect the creation of the transition metal borate catalyst systems of this invention as will be seen in the Examples.

The olefin esterification reaction in which the catalysts of this invention are useful is now described in more detail.

The olefin feedstocks may consist of any mono olefin having the double bond located anywhere within the molecule and mixtures of such olefins. The olefin may be an alpha or an internal olefin. Specific examples of suitable feedstocks include, but are not limited by, the following list: propylene, 1-butene, 2-butene, 1-pentene, 2-pentene, 1-hexene, 2-hexene, 3-hexene, heptenes, octenes, nonenes, decenes, undecenes, dodecenes, tridecanes such as 6-tridecene, tetradecenes such as 7-tetradecene, pentadecenes, hexadecenes, etc., and mixtures thereof. Preferably, the olefin has 3 to 16 carbon atoms.

Of course, molecular oxygen in a pure form or air is an essential co-reactant.

The co-reactant and solvent must be a compound capable of generating a carboxylate ion when it serves as a solvent. These compounds may be generally described as carboxylic acids or anhydrides. They may include materials such as acetic acid, acetic anhydride, carboxylic acids, etc., although acetic acid and acetic anhydride are the preferred solvents/co-reactants. Acetic acid is the preferred coreactant.

The conditions under which the reaction may be conducted include a temperature range of from 50° to 280° C. A preferred range is from 120° to 220° C. The pressure may be one atmosphere or higher. These conditions are much milder than many of those in the prior art discussed earlier.

An initiator may be optionally used to provide an initial source of free radicals. The use of a readily oxidizable initiator helps to start the oxidation as well as prevent a possible buildup of peroxides which would be dangerous. Aldehydes are suitable initiators with heptaldehyde being the preferred initiator. Usually a few drops are enough to be effective; i.e. quantities on the order of 1.0 ml. Peroxides and azo compounds are also used as initiators.

The invention will be further illustrated by the following examples which are not intended to limit the scope of the invention.

EXAMPLE 1

Preparation of Vanadyl-Cobalt Borate Catalyst System

Vanadyl sulfate (0.025 Mol) and cobalt nitrate (0.025 Mol) were dissolved in a minimum amount of hot water and added slowly to a vigorously stirred solution of sodium borate (0.10 Mol) in ~100 ml of hot (about 80° C.) water. The mixture was stirred for an additional 30 minutes at about 80° C. and then allowed to cool to room temperature. The solid was collected with suction and dried at 80° C. for three days. Analysis of the solid by Atomic Adsorption (AA) showed 19.3% cobalt; 2.02% vanadium, and 13.7% boron.

EXAMPLE 2

Zirconyl-Cobalt Borate Catalyst System

Zirconyl nitrate (0.025 Mol) and cobalt nitrate (0.025 Mol) were dissolved in a minimum amount of hot water and added slowly to a vigorously stirred solution of sodium borate (0.10 Mol) in ~100 ml of hot (about 80° C.) water. The mixture was stirred for an additional 30 minutes at 80° C. and then allowed to cool to room temperature. The solid mass was collected with suction and dried at 80° C. for three days. Analysis of the solid by AA showed 8.2% cobalt and 11.5% boron. Means were not available to determine the zirconium content.

EXAMPLES 3-9

Olefin Esterifications

A 1-liter 316 stainless steel glass-lined autoclave equipped with a magnetic stirrer was charged with 300 ml of glacial acetic acid and catalyst. The autoclave was sealed, 42 g of propylene pressured in, and the mixture heated to the desired temperature. Oxygen was added slowly to a pressure 50-100 psi higher than autogeneous pressure. The pressure was maintained by addition of oxygen from time to time (after such addition of oxygen there was a small exotherm) for the desired reaction time. The reaction mixture was then cooled to room temperature, the reactor vented and the contents analyzed by vapor phase chromatography. The results are shown in Table I.

Examples 5–7 show that combinations of transition metal borates are effective to catalyze the oxidative esterification of alkylenes.

TABLE III

ADDITIONAL EXAMPLES ILLUSTRATING THE INVENTION

| Ex. | Catalyst ID | (g) | Temp., °C. | Time, (Hr) | Approx. Conv. % | Esters Selectivity wt. % |
|---|---|---|---|---|---|---|
| 3 | $ZrO(BO_2)_2$ | 1.0 | 170 | 6 | 13 | 87.6 |
| 4[1] | $ZrO(BO_2)_2$ | 1.0 | 180 | 5 | 23 | 88.4 |
| 5 | $ZrO.Ni(BO_2)_2$ | 1.0 | 170 | 6 | 14 | 87.6 |
| 6[3] | $ZrO.Ni(BO_2)_2$ | 1.0 | 160 | 3 | 11 | 86.1 |
| 7[3] | $ZrO.CO(BO_2)_2$ | 1.0 | 160 | 3 | 9 | 84.9 |
| 8[1] | None | — | 160 | 5 | 4 | 83.2 |
| 9 | None | — | 160 | 5 | 4 | ~0 |

[1] 1.00 ml of heptaldehyde was also included as an initiator.
[2] This example employed the catalyst used in U.S. Pat. No. 4,221,916.
[3] 84 g of propylene was used in this example.

Many modifications may be made in the composition of this invention by those skilled in the art without departing from the spirit and scope of the invention which is defined only by the appended claims. For example, one skilled in the art could determine an exact combination of transition metal borates optimize the yield of a particular reaction product.

We claim:

1. A catalyst system of at least two transition metal borates comprising
   a. a transition metal borate where the transition metal is taken from the group consisting of Group IVB and Group VB of the Periodic Table, and
   b. a transition metal borate where the transition metal is taken from Group VIII of the Periodic Table.

2. The catalyst system of claim 1 in which
   a. the transition metal taken from the group consisting of Group IVB and Group VB elements of the Periodic Table is from the group consisting of vanadium and zirconium, and
   b. the transition metal taken from Group VIII of the Periodic Table is taken from the group consisting of cobalt and nickel.

3. The catalyst system of claim 2 in which the catalyst system is chosen from the group of combinations consisting of zirconyl borate/nickel borate, vanadyl borate/cobalt borate and zirconyl borate/cobalt borate.

* * * * *